US009603866B2

(12) United States Patent
Xu et al.

(10) Patent No.: US 9,603,866 B2
(45) Date of Patent: Mar. 28, 2017

(54) ANTI-FATIGUE COMPOSITION, FORMULATION AND USE THEREOF

(71) Applicant: Shang Hai Innovative Research Center of Traditional Chinese Medicine, Shanghai (CN)

(72) Inventors: Changjiang Xu, Shanghai (CN); Weiguo Jia, Shanghai (CN); Chunying Yu, Shanghai (CN); Wenjing Zhang, Shanghai (CN); Qiyuan Han, Shanghai (CN); Qiang Ge, Shanghai (CN); Qinlin Wang, Shanghai (CN); Zirong Yang, Shanghai (CN)

(73) Assignee: Shang Hai Innovative Research Center of Traditional Chinese Medicine, Shanghai (CN)

( * ) Notice: Subject to any disclaimer, the term of this patent is extended or adjusted under 35 U.S.C. 154(b) by 127 days.

(21) Appl. No.: 14/535,257

(22) Filed: Nov. 6, 2014

(65) Prior Publication Data
US 2015/0065452 A1 Mar. 5, 2015

Related U.S. Application Data

(62) Division of application No. 13/812,485, filed as application No. PCT/CN2011/001233 on Jul. 27, 2011, now abandoned.

(30) Foreign Application Priority Data

Jul. 27, 2010 (CN) .......................... 2010 1 0237955

(51) Int. Cl.
| | |
|---|---|
| *A61K 31/715* | (2006.01) |
| *A61K 31/575* | (2006.01) |
| *A61K 9/16* | (2006.01) |
| *A61K 9/20* | (2006.01) |
| *A61K 36/815* | (2006.01) |
| *A61K 47/10* | (2017.01) |
| *A61K 9/08* | (2006.01) |
| *A61K 9/48* | (2006.01) |

(52) U.S. Cl.
CPC ............ *A61K 31/715* (2013.01); *A23L 33/10* (2016.08); *A61K 9/08* (2013.01); *A61K 9/1623* (2013.01); *A61K 9/2018* (2013.01); *A61K 9/4858* (2013.01); *A61K 31/575* (2013.01); *A61K 36/815* (2013.01); *A61K 47/10* (2013.01)

(58) Field of Classification Search
None
See application file for complete search history.

(56) References Cited

FOREIGN PATENT DOCUMENTS

| | | | |
|---|---|---|---|
| CN | 1895256 A | 1/2007 | |
| CN | 1907061 A | 2/2007 | |
| CN | 101086459 A | 12/2007 | |
| CN | 101161246 A | 4/2008 | |
| CN | 101628071 A | * 1/2010 | ......... A61K 36/8945 |
| CN | 101890040 A | 11/2010 | |

OTHER PUBLICATIONS

Barton, D. L., Soori, G. S., Bauer, B. A., Sloan, J. A., Johnson, P. A., Figueras, C., . . . & Christensen, B. (2010). Pilot study of *Panax quinquefolius* (American ginseng) to improve cancer-related fatigue: a randomized, double-blind, dose-finding evaluation: NCCTG trial N03CA. Supportive Care in Cancer, 18(2), 179-187.*
Chiu, K., Chan, H. C., Yeung, S. C., Yuen, W. H., Zee, S. Y., Chang, R. C. C., & So, K. F. (2009). Modulation of microglia by Wolfberry on the survival of retinal ganglion cells in a rat ocular hypertension model. Journal of ocular biology, diseases, and informatics, 2(3), 127-136.*
Cui, J. F. (1995). Identification and quantification of ginsenosides in various commercial ginseng preparations. European journal of pharmaceutical sciences, 3(2), 77-85.*
Wang, C. C., Chang, S. C., Inbaraj, B. S., & Chen, B. H. (2010). Isolation of carotenoids, flavonoids and polysaccharides from Lycium barbarum L. and evaluation of antioxidant activity. Food Chemistry, 120(1), 184-192.*
International Search Report and Written Opinion received for PCT Patent Application No. PCT/CN2011/001233 mailed on Nov. 3, 2011, 23 pages.
International Preliminary Report on Patentability received for PCT Patent Application No. PCT/CN2011/001233, issued on Jan. 29, 2013, 15 pages.
Non-Final Office Action received for U.S. Appl. No. 13/812,485, mailed on Jul. 18, 2013, 16 pages.
Final Office Action received for U.S. Appl. No. 13/812,485, mailed on Feb. 13, 2014, 13 pages.
Non Final Office Action received for U. S. Appl. No. 13/812,485, mailed on Aug. 8, 2014, 12 pages.
Fukuda et al., "The Chronic Fatigue Syndrome: A Comprehensive Approach to Definition and Study", Annals of Internal Medicine, vol. 121, No. 12, Dec. 15, 1994, pp. 953-959.
Holmes et al., "Chronic Fatigue Syndrome: A Working Case Definition", Annals of Internal Medicine, vol. 108, No. 3, Mar. 1988, pp. 387-389.
Luo et al., "Effect of Lycium Barbarum Polysaccharides on Anti-fatigue in Mice", Acta Academiae Medicinae Hubei, vol. 20, No. 4, Oct. 1999, pp. 265-269.

(Continued)

*Primary Examiner* — Shaojia Anna Jiang
*Assistant Examiner* — Dale R Miller
(74) *Attorney, Agent, or Firm* — Morrison & Foerster LLP

(57) ABSTRACT

An anti-fatigue composition consisting of 20(S)-protopanoxadiol and *lycium barbarum* polysaccharide. Experiments prove that the composition exhibits a significant anti-fatigue effect. In comparison with the effect attained by the single use of *lycium barbarum* polysaccharide or 20(S)-protopanoxadiol, the combined use of 20(S)-protopanoxadiol and *lycium barbarum* polysaccharide exerts an obvious synergistic effect.

6 Claims, No Drawings

(56) References Cited

OTHER PUBLICATIONS

Luo et al., "Lycium Bbarbarum Polysaccharides Induce Apoptosis in Human Prostate Cancer Cells and Inhibits Prostate Cancer Growth in a Xenograft Mouse Model of Human Prostate Cancer", Journal of Medicinal Food, vol. 12, No. 4, Aug. 2009, pp. 695-703.
Li et al., "Effect of the Lycium Barbarum Polysaccharides on Age-Related Oxidative Stress in Aged Mice", Journal of Ethnopharmacology, vol. 111, No. 3, 2007, pp. 504-511.
Pan et al., "Antifatigue Effects and Immune Function Assessment of the Fruit of Lycium Barbaruml", Shanghai Journal of Preventive Medicine, vol. 15, No. 8, Aug. 15, 2003, pp. 377-379.
Wang et al., "Experimental Study on the Anti-Fatigue Action of Wolfberry Fruit", China Tropical Medicine, vol. 6, No. 8, Aug. 6, 2006, pp. 1523,1522.
Wang et al., "20(S)-25-Methoxyl-Dammarane-3β, 12β, 20-Triol, a Novel Natural Product for Prostate Cancer Therapy: Activity in Vitro and in Vivo and Mechanisms of Action", British Journal of Cancer, vol. 98, No. 4, 2008, pp. 792-802.
Zhou et al., "Experimental Study on Effect of Panaxadiol, Panaxatriol on Students' Intelligence and Emotion", Journal of Shenyang Institute of Physical Education, No. 3, 1998, pp. 11-14.

\* cited by examiner

ANTI-FATIGUE COMPOSITION, FORMULATION AND USE THEREOF

CROSS REFERENCE TO RELATED APPLICATIONS

This application is a divisional application of U.S. application Ser. No. 13/812,485, filed on Jul. 27, 2011, which is a U.S. National Phase patent application of PCT/CN2011/001233, filed Jul. 27, 2011, and both of which are hereby incorporated by reference in the present disclosure in their entireties; and PCT/CN2011/001233 claims priority to Chinese Patent Application No. 201010237955.0, filed Jul. 27, 2010.

TECHNICAL FIELD

The present invention belongs to medicine field, particularly relates to an anti-fatigue composition, formulation and use thereof.

BACKGROUND ART

At the fifth International Biochemistry of Exercise Congress in 1982, the fatigue is defined that: the body's physiological processes can not maintain its function at a certain degree or the organs can not maintain its predetermined exercise intensity.

Fatigue is classified as central nervous system fatigue, nerve-muscle joint fatigue and peripheral fatigue of the limbs. Fatigue is a comprehensive physiological process involving many physiological and biochemical factors, and it's a normal physiological phenomenon inevitably occurring at a certain stage of the mental activity or physical activity of the body. It marks a temporary decline of the original work ability of the body, and may be an indication indicating the body develops to an injury status.

At present people are paying more attention to the Chronic Fatigue Syndrome (CFS). CFS is a group of syndrome, which takes long-term durable fatigue as prominent manifestation, accompanying with non-specific manifestations of low fever, headache, sore throat, muscle and joint pain, inattention, memory decline, sleep disorders, depression and the like, generally nothing abnormal is detected in physical examination and routine examination (Holmes G O, Kaplan J E, Gantz N M, et al. Chronic Fatigue Syndrome: A Working Case Definition. Ann Intern Med, 1988, 108(3): 387-389; Fukuda K, Straus S E, Hickie I, et al. The Chronic Fatigue Syndrome: A Comprehensive Approach to Definition and Study. Ann Intern Med, 1994, 121(12): 953-959). CFS is more likely to happen in people at the age group of 20-50 years old, and more common in women. CFS significantly affects work and living of a subject and gains great concern in the medical field.

There are many causes which may lead to fatigue, such as working environment, diet habit and lifestyle, especially the diseases, which may bring to a subject mental stress, physical exertion, and lowered resistance in various functions of the body; as well as the physical exertion caused by drugs, which is easy to lead to fatigue. For example, the symptom of fatigue is normally seen in a cancer or mental patient who is subjected to a treatment.

Currently, the widely used methods of relieving fatigue adjust the body function by sleep and recuperation etc. On the other hand, the body function can be improved by recuperating with external materials. However, there is no anti-fatigue medicament or food with significant effect available in the current market.

*Lycium chinense*, which is ripe fruit of a deciduous small shrub of *Lycium* plants in Solanaceae family, is a traditional Chinese herb medicine having effects of strengthening with tonics, replenishing vital essence, dispelling rheumatism, invigorating Yang, strengthening muscles and bones etc. It is recorded in an ancient Chinese medical book named Dietetic Materia Medica that, ripe fruits of *Lycium chinense* have the functions of "strengthening muscles to endure hard work, dispelling rheumatism, nourishing and benefiting muscles and bones, benefiting human body, and removing asthenic disease". Research of modern pharmacology proves that, the active ingredient of *Lycium chinense* fruits is *lycium barbarum* polysaccharide which has the functions of reducing the level of blood sugar and blood fat, improving immunity, antioxidation and anti-fatigue etc. At present, there are literatures reporting the anti-fatigue effect of *Lycium chinense* fruits as follows:

LUO Qiong et al. reports the influence of *lycium barbarum* polysaccharide on the anti-fatigue effect of mice, experiments show that *lycium barbarum* polysaccharide is the main ingredient for anti-fatigue effect of *Lycium chinense* fruits (LUO Qiong, YAN Jun and ZHANG Shenghua. Influence of *Lycium Barbarum* Polysaccharide on the Anti-fatigue Effect for Mice. Journal of Hubei Medical University, 1999, No. 4); WANG Yanwu et al. reports that *lycium barbarum* polysaccharide has anti-fatigue effect (WANG Yanwu, FU Weizhong, TAN Zongyan et al. Experimental Research on Anti-fatigue Effect of *Lycium Barbarum* Polysaccharide. China Tropical Medicine, 2006, No. 8, August 2006,(6):8); PAN Jingyi et al. reports that *Lycium chinense* fruits has functions of anti-fatigue, improving exercise tolerance and immunity for mice (Experimental Research on Anti-fatigue and Improving Immunity Effects of *Lycium chinense* Fruits, Shanghai Journal of Preventive Medicine, 2003, Vol. 15, No. 8).

Protopanoxadiol is aglycon of ginsenoside diol set, including 20(S)-protopanoxadiol and 20(R)-protopanoxadiol, which are enantiomers to each other and are represented by the following formulas.

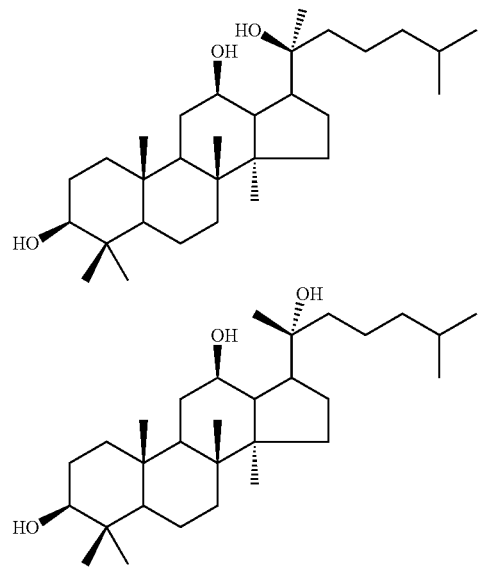

20(S)-protopanoxadiol, which does not occur naturally, is a metabolite of ginsenoside in the body. Chinese Patent Application No. CN200610027507.1 discloses the anti-depression activity of 20(S)-protopanoxadiol; Chinese Patent Application No. CN200610027508.6 discloses the anti-intestinal cancer activity of 20(S)-protopanoxadiol; Chinese Patent Application No. CN200610131959.4 discloses novel use of ginsenoside Rh2 for anti-fatigue; Chinese Patent Application No. CN200610017063.3 discloses anti-fatigue effect of a composition comprising ginseng, coffee and tea. The single use of 20(S)-protopanoxadiol for anti-fatigue has not been reported yet.

Although *lycium barbarum* polysaccharide has a certain anti-fatigue effect, such effect needs to be improved. Until now, there is no patent or literature reporting using 20(S)-protopanoxadiol and *lycium barbarum* polysaccharide for anti-fatigue.

CONTENTS OF THE INVENTION

The object of the invention is to provide an anti-fatigue composition.

Another object of the invention is to provide a formulation comprising the composition.

Still another object of the invention is to provide use of the composition.

The anti-fatigue composition according to the invention consists of 20(S)-protopanoxadiol and *lycium barbarum* polysaccharide.

In the composition, the weight ratio of the 20(S)-protopanoxadiol and *lycium barbarum* polysaccharide is 0.01-50 to 60-480.

Preferably in the composition, the weight ratio of the 20(S)-protopanoxadiol and *lycium barbarum* polysaccharide is 0.01-5 to 120-480.

The invention also provides a formulation comprising the above composition, wherein the formulation consists of the composition and pharmaceutically acceptable excipient, and the formulation may be in form of tablets, pills, capsules, granules or oral solution.

The pharmaceutically acceptable excipient is one or more selected from the group consisting of filler, disintegrating agent, adhesive, lubricant, diluent, sweetener, flavoring agent, coloring agent, emulsifier and suspending agent.

The filler is one or more selected from the group consisting of lactose, sucrose, dextrin, mannitol, sorbitol, microcrystalline cellulose and starch.

The disintegrating agent is selected from the group consisting of microcrystalline cellulose, starch, low substituted hydroxypropyl cellulose and crosslinked polyvinylpyrrolidone.

The adhesive is selected from the group consisting of polyvinylpyrrolidone, starch and ethanol.

The lubricant is selected from the group consisting of magnesium stearate, sodium lauryl sulfate, silica and talc.

The diluent is selected from the group consisting of water, ethanol, propylene glycol and glycerol.

The sweetener is one or more selected from the group consisting of glucose, fructose, sucrose, maltose, starch sugar and lactose.

The instant invention further provides use of the above composition and formulation thereof in the preparation of medicaments and healthcare products for anti-fatigue.

The fatigue may result from various causes.

Preferably the fatigue results from diseases.

More preferably the fatigue results from cancer or depression.

Experiments show that the composition according to the invention which consists of 20(S)-protopanoxadiol and lycium barbarum polysaccharide has a synergistic effect in anti-fatigue.

SPECIFIC MODE FOR CARRYING OUT THE INVENTION

The following Examples are intended to further illustrate the present invention without limiting its scope.

EXPERIMENTAL EXAMPLE 1

Effect of Composition Consisting of 20(S)-protopanoxadiol and *Lycium barbarum* Polysaccharide on Mice Burden Swimming Time According to the Technical Standards for Testing & Assessment of Health Food issued by the Ministry of Health, P. R. China, function and biochemistry indexes assessment of the mixture of 20(S)-protopanoxadiol and *lycium barbarum* polysaccharide on the function of relieving physical fatigue is conducted; the detailed method is given as follows:

1. Experimental animals: ICR mice, male, 18-22 g, provided by Shanghai Slack laboratory animal Co. Ltd., license number: SCXK (Shanghai) 2007-0005;

2. Experimental Drugs:

20(S)-protopanoxadiol: provide by Shanghai Innovative Research Center of Traditional Chinese Medicine, batch number: 20050606-1, purity: 94%; *lycium barbarum* polysaccharide: provided by Shanghai KangZhou Fungi Extract Co. Ltd., polysaccharide content≥30%.

To 20(S)-protopanoxadiol is added a small amount of 0.3% CMC-Na, followed by grinding to form a suspension and diluting with CMC-Na to a desired concentration. Then *lycium barbarum* polysaccharide is added to the 20(S)-protopanoxadiol suspension to form a composition with a certain concentration.

3. Experimental groups: the mice are randomly divided into 19 groups by weight, 20 mice per each group; the detailed groups are as follows:
   normal (solvent) control
   20(S)-protopanoxadiol: 0.01 mg/kg
   20(S)-protopanoxadiol: 0.5 mg/kg
   20(S)-protopanoxadiol: 1 mg/kg
   *lycium barbarum* polysaccharide: 120 mg/kg
   *lycium barbarum* polysaccharide: 240 mg/kg
   *lycium barbarum* polysaccharide: 480 mg/kg
   20(S)-protopanoxadiol+*lycium barbarum* polysaccharide: 0.01 mg/kg+120 mg/kg
   20(S)-protopanoxadiol+*lycium barbarum* polysaccharide: 0.01 mg/kg+240 mg/kg
   20(S)-protopanoxadiol+*lycium barbarum* polysaccharide: 0.01 mg/kg+480 mg/kg
   20(S)-protopanoxadiol+*lycium barbarum* polysaccharide: 0.5 mg/kg+120 mg/kg
   20(S)-protopanoxadiol+*lycium barbarum* polysaccharide: 0.5 mg/kg+240 mg/kg
   20(S)-protopanoxadiol+*lycium barbarum* polysaccharide: 0.5 mg/kg+480 mg/kg
   20(S)-protopanoxadiol+*lycium barbarum* polysaccharide: 1 mg/kg+120 mg/kg
   20(S)-protopanoxadiol+*lycium barbarum* polysaccharide: 1 mg/kg+240 mg/kg
   20(S)-protopanoxadiol+*lycium barbarum* polysaccharide: 1 mg/kg+480 mg/kg 20(S)-protopanoxadiol+*lycium barbarum* polysaccharide: 5 mg/kg+120 mg/kg 20(S)-protopanoxadiol+*lycium barbarum* polysaccharide: 5 mg/kg+240 mg/kg 20(S)-protopanoxadiol+*lycium barbarum* polysaccharide: 5 mg/kg+480 mg/kg 4. Experimental Method:

0.2 ml/10 g of drug is administrated by gavage every day; for normal control group, 0.2 ml/10 g of distilled water is administrated by gavage every day; once a day, 30 days in total.

30 minutes after the last time of administrating drug, the end of the tail of each mouse is loaded with copper wires corresponding to 6% of its body weight, then the mouse is put in a swimming box to swim, the time from start of swimming to death of the mouse is recorded, i.e. the mice burden swimming time; the water depth in the swimming box is 30 cm or more, and water temperature is 23+1.0° C.

5. Statistical data processing: t-test is conducted to calculate P value, Jin Zhengjun formula is used to conduct combined medication analysis.

6. Experimental Results:

Mice burden swimming test is conducted with drug dosages of 0.01-5 mg/kg of 20(S)-protopanoxadiol and 120-480 mg/kg of *lycium barbarum* polysaccharide, the results are shown in Table 1:

The results in Table 1 show that: as compared with normal group, *lycium barbarum* polysaccharide can prolong the mice burden swimming time at different levels, the composition consisting of 20(S)-protopanoxadiol and *lycium barbarum* polysaccharide in a weight ratio of 0.01-5 to 120-480 can prolong the mice burden swimming time at different levels ($P<0.01$, $P<0.05$); as compared with the effect of 20(S)-protopanoxadiol or *lycium barbarum* polysaccharide, the composition consisting of 20(S)-protopanoxadiol and *lycium barbarum* polysaccharide in a weight ratio of 0.01-5 to 120-480 can also prolong the mice burden swimming time at different levels ($P<0.01$, $P<0.05$).

Conclusion: combined use of 20(S)-protopanoxadiol and *lycium barbarum* polysaccharide exerts an obvious synergistic effect.

EXPERIMENTAL EXAMPLE 2

Effects of the Combined Dosage of 20(S)-protopanoxadiol and *Lycium barbarum* Polysaccharide on Mice Burden Swimming Time Other than the combined dosage of Experimental example 1, the range of combined dosage is enlarged to conduct multi-batch experiments. The experimental animals, drugs and method are the same as those of Experimental example 1, and the final results are shown in Table 2:

TABLE 1

Effect of 20(S)-protopanoxadiol and lycium barbarum polysaccharide on mice burden swimming time ($\bar{x} \pm S$)

| Groups | Dosage (mg/kg) | Animal number | Animal weight start/finish (g) | Swimming time (s) | Change rate of swimming time (%) |
|---|---|---|---|---|---|
| normal control group | solvent | 20 | 21.7/39.3 | 620 ± 285 | |
| 20(S)-protopanoxadiol | 0.01 | 20 | 21.6/39.2 | 640 ± 275 | 1.5 |
| 20(S)-protopanoxadiol | 0.5 | 20 | 21.8/38.8 | 660 ± 268 | 1.9 |
| 20(S)-protopanoxadiol | 1 | 20 | 21.7/38.7 | 658 ± 296 | 2.2 |
| 20(S)-protopanoxadiol | 5 | 20 | 21.8/38.9 | 640 ± 286 | 1.5 |
| lycium barbarum polysaccharide | 120 | 20 | 21.7/39.5 | 783 ± 189** | 26.4 |
| lycium barbarum polysaccharide | 240 | 20 | 21.8/39.7 | 794 ± 385** | 28.1 |
| lycium barbarum polysaccharide | 480 | 20 | 21.8/38.8 | 766 ± 282* | 23.5 |
| 20(S)-protopanoxadiol + lycium barbarum polysaccharide | 0.01 + 120 | 20 | 21.7/39.5 | 798 ± 235** | 28 |
| 20(S)-protopanoxadiol + lycium barbarum polysaccharide | 0.01 + 240 | 20 | 21.8/39.2 | 843 ± 283** | 40 |
| 20(S)-protopanoxadiol + lycium barbarum polysaccharide | 0.01 + 480 | 20 | 21.9/38.8 | 865 ± 298** | 42.6 |
| 20(S)-protopanoxadiol + lycium barbarum polysaccharide | 0.5 + 120 | 20 | 21.8/39.3 | 853 ± 229** | 35.5 |
| 20(S)-protopanoxadiol + lycium barbarum polysaccharide | 0.5 + 240 | 20 | 21.8/39.1 | 898 ± 322** | 44.8 |
| 20(S)-protopanoxadiol + lycium barbarum polysaccharide | 0.5 + 480 | 20 | 21.8/38.7 | 923 ± 224** | 48.9 |
| 20(S)-protopanoxadiol + lycium barbarum polysaccharide | 1 + 120 | 20 | 21.8/39.4 | 842 ± 252** | 35.78 |
| 20(S)-protopanoxadiol + lycium barbarum polysaccharide | 1 + 240 | 20 | 21.9/39.1 | 993 ± 289** | 60.2 |
| 20(S)-protopanoxadiol + lycium barbarum polysaccharide | 1 + 480 | 20 | 21.8/38.3 | 1063 ± 342** | 71.4 |
| 20(S)-protopanoxadiol + lycium barbarum polysaccharide | 5 + 120 | 20 | 21.7/39.2 | 875 ± 279** | 36.42 |
| 20(S)-protopanoxadiol + lycium barbarum polysaccharide | 5 + 240 | 20 | 21.9/38.8 | 1069 ± 243** | 62.8 |
| 20(S)-protopanoxadiol + lycium barbarum polysaccharide | 5 + 480 | 20 | 21.8/39.0 | 1185 ± 242** | 75.1 |

Note:
compared with normal control group, *$P < 0.05$, **$P < 0.01$

TABLE 2

Effect of 20(S)-protopanoxadiol and lycium barbarum polysaccharide on mice burden swimming time

| Groups | Dosage (mg/kg) | Swimming time change rate (%) |
|---|---|---|
| normal control group | solvent | 0 |
| 20(S)-protopanoxadiol | 0.01 | 1.5 |
| 20(S)-protopanoxadiol | 0.5 | 1.9 |
| 20(S)-protopanoxadiol | 1 | 2.2 |
| 20(S)-protopanoxadiol | 3 | 1.6 |
| 20(S)-protopanoxadiol | 6.25 | 1.4 |
| 20(S)-protopanoxadiol | 12.5 | 3.4 |
| 20(S)-protopanoxadiol | 25 | 6.9 |
| 20(S)-protopanoxadiol | 50 | 12.4* |
| lycium barbarum polysaccharide | 10 | 7.5 |
| lycium barbarum polysaccharide | 30 | 8.1 |
| lycium barbarum polysaccharide | 60 | 10.5 |
| lycium barbarum polysaccharide | 120 | 26.4** |
| lycium barbarum polysaccharide | 240 | 28.1** |
| lycium barbarum polysaccharide | 480 | 23.5* |
| 20(S)-protopanoxadiol + lycium barbarum polysaccharide | 0.01 + 60 | 21.3* |
| 20(S)-protopanoxadiol + lycium barbarum polysaccharide | 0.01 + 120 | 28** |
| 20(S)-protopanoxadiol + lycium barbarum polysaccharide | 0.01 + 240 | 40** |
| 20(S)-protopanoxadiol + lycium barbarum polysaccharide | 0.01 + 480 | 42.6** |
| 20(S)-protopanoxadiol + lycium barbarum polysaccharide | 0.5 + 60 | 25.5** |
| 20(S)-protopanoxadiol + lycium barbarum polysaccharide | 0.5 + 120 | 35.5** |
| 20(S)-protopanoxadiol + lycium barbarum polysaccharide | 0.5 + 240 | 44.8** |
| 20(S)-protopanoxadiol + lycium barbarum polysaccharide | 0.5 + 480 | 48.9** |
| 20(S)-protopanoxadiol + lycium barbarum polysaccharide | 1 + 60 | 22.6* |
| 20(S)-protopanoxadiol + lycium barbarum polysaccharide | 1 + 120 | 35.78** |
| 20(S)-protopanoxadiol + lycium barbarum polysaccharide | 1 + 240 | 60.2** |
| 20(S)-protopanoxadiol + lycium barbarum polysaccharide | 1 + 480 | 71.4** |
| 20(S)-protopanoxadiol + lycium barbarum polysaccharide | 3 + 60 | 22.8* |
| 20(S)-protopanoxadiol + lycium barbarum polysaccharide | 3 + 120 | 36.8** |
| 20(S)-protopanoxadiol + lycium barbarum polysaccharide | 3 + 240 | 38.7** |
| 20(S)-protopanoxadiol + lycium barbarum polysaccharide | 6.25 + 60 | 17.6* |
| 20(S)-protopanoxadiol + lycium barbarum polysaccharide | 6.25 + 120 | 22.5* |
| 20(S)-protopanoxadiol + lycium barbarum polysaccharide | 6.25 + 240 | 32.9** |
| 20(S)-protopanoxadiol + lycium barbarum polysaccharide | 12.5 + 120 | 26.6** |
| 20(S)-protopanoxadiol + lycium barbarum polysaccharide | 25 + 60 | 38.1** |
| 20(S)-protopanoxadiol + lycium barbarum polysaccharide | 25 + 120 | 41.7** |
| 20(S)-protopanoxadiol + lycium barbarum polysaccharide | 25 + 240 | 50.1** |
| 20(S)-protopanoxadiol + lycium barbarum polysaccharide | 25 + 480 | 32.9** |
| 20(S)-protopanoxadiol + lycium barbarum polysaccharide | 50 + 60 | 41.9** |
| 20(S)-protopanoxadiol + lycium barbarum polysaccharide | 50 + 120 | 42.8** |
| 20(S)-protopanoxadiol + lycium barbarum polysaccharide | 50 + 240 | 48.1** |
| 20(S)-protopanoxadiol + lycium barbarum polysaccharide | 50 + 480 | 55.5** |

Note:
compared with normal control group, *P < 0.05, **P < 0.01

The results in Table 2 show that: as compared with normal control group, single use of 20(S)-protopanoxadiol has no significant effect on mice swimming time (P>0.05), use of 120-480 mg/kg of *lycium barbarum* polysaccharide alone can prolong mice swimming time at different levels (P<0.05, P<0.01), the composition of 20(S)-protopanoxadiol and *lycium barbarum* polysaccharide in a weight ratio of 0.01-50 to 60-480 can apparently prolong mice burden swimming time (P<0.01 or P<0.05); as compared with the effect of use of 20(S)-protopanoxadiol or *lycium barbarum* polysaccharide alone, the effect of combined use of 20(S)-protopanoxadiol and *lycium barbarum* polysaccharide on mice burden swimming time is bigger than the sum of the effects of single use of the two, that is to say, although 20(S)-protopanoxadiol has no effect on mice burden swimming endurance, combined use of 20(S)-protopanoxadiol and *lycium barbarum* polysaccharide exerts apparent and unexpected synergistic effect.

Conclusion: combined use of 20(S)-protopanoxadiol and *lycium barbarum* polysaccharide exerts apparent synergistic effect.

EXAMPLE 1

Tablets of the Anti-Fatigue Composition 500 g of lactose is added to 4 g of 20(S)-protopanoxadiol and 2000 g of *lycium barbarum* polysaccharide, followed by mixing uniformly, taking 70% ethanol as adhesive, granulating, drying, and then adding 10 g of magnesium stearate and tabletting to obtain tablets.

EXAMPLE 2

Capsules of the Anti-Fatigue Composition 200 g of lactose is added to 8 g of 20(S)-protopanoxadiol and 2000 g of *lycium barbarum* polysaccharide, followed by mixing uniformly, taking 70% ethanol as adhesive, granulating and filling in capsule to obtain the capsules.

EXAMPLE 3

Oral Solution of the Anti-Fatigue Composition 100 g of Tween-80 is added to 16 g of 20(S)-protopanoxadiol and 2000 g of *lycium barbarum* polysaccharide, followed by grinding to form primary emulsion, adding water to a volume of 5000 ml to obtain the oral solution.

INDUSTRIAL APPLICABILITY

The anti-fatigue composition according to the invention consists of 20(S)-protopanoxadiol and *lycium barbarum* polysaccharide. The experiments show that the composition can apparently prolong the swimming time of mice with weight loading, i.e. it exerts an obvious synergistic effect in anti-fatigue. In comparison with the effect attained by the single use of *lycium barbarum* polysaccharide or 20(S)-protopanoxadiol, the combined use of 20(S)-protopanoxadiol and *lycium barbarum* polysaccharide exerts an obvious synergistic effect. The composition according to the invention can be used in the preparation of anti-fatigue medicaments and healthcare products; it provides a novel method of relieving fatigue and possesses industrial applicability.

What is claimed is:

1. A method for relieving fatigue, comprising administering a formulation, wherein the formulation consists of 20(S)-protopanoxadiol, lycium barbarum polysaccharide and one or more pharmaceutically acceptable excipients.

2. The method of claim 1, wherein the fatigue results from various causes.

3. The method of claim 1, wherein the fatigue results from diseases.

4. The method of claim 1, wherein the fatigue results from cancer or depression.

5. The method of claim 1, wherein the formulation is in form of a tablet, pill, capsule, granule or oral solution.

6. The method of claim 1, wherein the one or more pharmaceutically acceptable excipients are selected from the group consisting of filler, disintegrating agent, adhesive, lubricant, diluent, sweetener, flavoring agent, coloring agent, emulsifier, and suspending agent.

* * * * *